US009029131B2

(12) United States Patent
Richter et al.

(10) Patent No.: US 9,029,131 B2
(45) Date of Patent: May 12, 2015

(54) AUTOMATIC MICROFLUIDIC PROCESSOR

(75) Inventors: Andreas Richter, Dresden (DE); Stephan Klatt, Dresden (DE); Tobias Wage, Dresden (DE)

(73) Assignee: Technische Universität Dresden, Dresden (DE)

( * ) Notice: Subject to any disclaimer, the term of this patent is extended or adjusted under 35 U.S.C. 154(b) by 1446 days.

(21) Appl. No.: 12/446,979

(22) PCT Filed: Oct. 23, 2007

(86) PCT No.: PCT/DE2007/001905
§ 371 (c)(1), (2), (4) Date: Oct. 11, 2009

(87) PCT Pub. No.: WO2008/049413
PCT Pub. Date: May 2, 2008

(65) Prior Publication Data

US 2010/0151561 A1 Jun. 17, 2010

(30) Foreign Application Priority Data

Oct. 27, 2006 (DE) ........................ 10 2006 051 535

(51) Int. Cl.
*C12M 1/34* (2006.01)
*B01L 3/00* (2006.01)
(Continued)

(52) U.S. Cl.
CPC ..... *B01L 3/50273* (2013.01); *B01L 2400/0672* (2013.01); *B01F 5/0646* (2013.01); *B01F 5/0647* (2013.01); *B01F 13/0059* (2013.01);
(Continued)

(58) Field of Classification Search
CPC ................ B01L 2400/0672; B01L 2400/0677; B01L 3/502715; B01L 3/50273; B01L 3/502738; B01L 2300/087; B01L 2200/10
USPC ................................ 435/288.5; 422/502–505
See application file for complete search history.

(56) References Cited

U.S. PATENT DOCUMENTS 5,224,843 A 7/1993 van Lintel
5,659,171 A 8/1997 Young et al.
(Continued)

FOREIGN PATENT DOCUMENTS

DE 10157317 A1 6/2003
DE 102004062893 A1 6/2006
WO WO 2004023105 A2 * 3/2004

OTHER PUBLICATIONS

English language machine translation of DE10157317 (Jun. 5, 2003).*

Pal, R et al: Phase Change Microvalve for Integrated Devices; Anal. Chem. 76 (2004) 13; pp. 3740-3748 (mentioned in instant specification, p. 3, lines 3-4).

Richter, A et al: Electronically Controllable Microvalves Based on Smart Hydrogels: Magnitudes and Potential Applications; J. Microelectromech. Syst. 12 (2003) 5, pp. 748-753 (mentioned in instant specification, p. 5, lines 23-25).

(Continued)

*Primary Examiner* — William H Beisner
(74) *Attorney, Agent, or Firm* — Gudrun E. Huckett

(57) ABSTRACT

In a microfluidic processor with integrated active elements for handling process media, the active elements act by changes in their volume, swelling degree, material composition, their strength and/or viscosity. The procedures to be performed are defined already by the constructive configuration of the microfluidic processor by an appropriate logic connection of the individual active elements defined in their function, by the sequence of the temporal activation of the individual elements, and with respect to their processing speed and their precision. The process is enabled by action of a substantially non-directional collectively acting environmental parameter, in particular, the presence of a solvent or environmental temperature or both.

17 Claims, 6 Drawing Sheets

(51) Int. Cl.
*B01F 5/06* (2006.01)
*B01F 13/00* (2006.01)
*B01L 7/00* (2006.01)

(52) U.S. Cl.
CPC ............. *B01L 3/502738* (2013.01); *B01L 7/52* (2013.01); *B01L 2200/10* (2013.01); *B01L 2300/0816* (2013.01); *B01L 2300/0867* (2013.01); *B01L 2300/087* (2013.01); *B01L 2400/0421* (2013.01); *B01L 2400/0481* (2013.01); *B01L 2400/0677* (2013.01)

(56) References Cited

U.S. PATENT DOCUMENTS

| | | | | |
|---|---|---|---|---|
| 6,283,718 | B1 | 9/2001 | Prosperetti et al. | |
| 6,488,872 | B1 * | 12/2002 | Beebe et al. | 264/31 |
| 6,536,476 | B2 | 3/2003 | Ueno et al. | |
| 7,479,135 | B2 | 1/2009 | Richter et al. | |
| 8,337,777 | B2 * | 12/2012 | Nurse et al. | 422/503 |
| 2003/0143122 | A1 | 7/2003 | Sander | |
| 2005/0250200 | A1 * | 11/2005 | Nakajima et al. | 435/287.2 |
| 2006/0102483 | A1 | 5/2006 | Chuang | |

OTHER PUBLICATIONS

Te Nijenhuis, K.: Thermoreversible Networks; Adv. Polymer Sci. 130, Springer-Verlag Berlin Heidelberg New York 1997; chapters 10 and 11 (mentioned in instant specification, p. 6, lines 1-3).

Arndt, K.-F. et al: Application of Sensitive Hydrogels in Flow Control; Polym. Adv. Technol. 11 (2000) pp. 496-505 (mentioned in instant specification, p. 10, lines 17-18).

Baldi A et al: A hydrogel-actuated environmentally sensitive microvalve for active flow control; Journal of Microelectrochemical Systems; IEEE, Service Center; Piscataway, NJ USA, vol. 12, No. 5 Oct. 2003, pp. 613-621 (see international search report).

Ming Lei et al: A hydrogel-actuated microvalve for smart flow control; San Francisco, CA, USA Sep. 1-5, 2004; Piscataway, NJ USA, IEEE, USA, vol. 13, Sep. 1, 2004, pp. 2041-2044 (see international search report).

Melin J et al: A liquid-triggered liquid microvalve for on-chip flow control; Sensors and Actuators B; Elsevier Sequoia, S.A., Lausanne, CH; vol. 100, No. 3, May 15, 2004, pp. 475-480 (see international search report).

* cited by examiner

AUTOMATIC MICROFLUIDIC PROCESSOR

BACKGROUND OF THE INVENTION

The invention concerns an automatic microfluidic processor with integrated active elements.

In (bio)chemical, pharmaceutical, and biomedical industry there is a growing need with respect to miniaturizing fluidic process technology. This desire is fulfilled by microfluidic devices. When these devices by function integration realize more or less complex biological, biochemical or chemical processes, they are referred to as microfluidic processors or also “labs on a chip” (LOC), chip labs or “micro total analysis systems (μTAS).

The LOC concept offers multiple advantages. The reduction of fluid volumes enables analysis of smallest sample quantities and a frugal use of reagents and samples that are often precious, rare, harmful or dangerous. In this way, also higher throughput rates are possible because, as a result of the minimal quantities, shortened preparation time, mixing time, and reaction time are required while the energy consumption is minimized. As a result of reduced system response times, process control can also be facilitated.

As a whole, the LOC configurations enable important process rationalizations in that they significantly shorten the processing time and therefore increase the possible throughput and decrease the quantities of required media (probands, analytes, agents, auxiliaries). Moreover, they should enable even non-experts to perform complex examinations, in order to, for example, provide policemen, general practitioners or controlling agencies e.g. food inspectors with quick access to important results.

Despite the apparent advantages, real LOC applications are available only in exceptional cases. The reasons are primarily of economic nature because the rationalizations do not outweigh the excess technological expenditure. In order to achieve economic efficiency, it must be analyzed which partial processes possess the appropriate rationalization potential.

PRIOR ART

The typical structure of biological, biochemical or chemical processes comprises the tasks of sample preparation, sample handling, and sample reaction or sample analysis in specific forms and combinations, respectively. Currently, mainly on-chip integration of the sample preparation as well as reaction or analysis are realized. The economic advantages resulting from the rationalization of these partial processes generally are not found to be satisfactory, however.

Enormous rationalization potential resides in sample handling because it is particularly time-consuming and labor-intensive. Because of its problematic on-chip integration, sample handling currently is done outside the chip either manually or by means of special apparatus, such as diluters, injection pumps, pipetting devices and the like. As a result of its primarily manual character, these tasks in practice are the number 1 source of errors.

The miniaturizable, electronically controlled fluidic drives (pumps) and switching element (valves) that are definitely available in a multitude of variants have disadvantages in such a way that either they cannot be incorporated economically into a lab-on-a-chip configuration or have unacceptable utilization properties.

Active fluidic elements on the basis of solid-state actuators such as piezo-actuators (U.S. Pat. No. 5,224,843, U.S. 2003/143122) and shape memory actuators (U.S. Pat. No. 5,659, 171) can be miniaturized well as individual elements but have a complex configuration, are limited to certain materials that are usually not plastic-based, and must therefore be manufactured separately. A possible hybrid integration (for example, adhesively connecting the elements on the LOC) is generally not economical.

Converters that are based on changes of the aggregate state can be integrated with partially minimal actions into the layout of the channel structure support and are therefore mostly compatible with manufacturing processes of the shaped plastic parts of the channel structure support. For example, melting elements (R. Pal et al., Anal. Chem. 76 (2004) 13, pp. 3740-3748) and freezing elements (U.S. Pat. No. 6,536,476) as well as thermal bubble generators (U.S. Pat. No. 6,283,718) are known.

However, converters based on aggregate state changes have some unacceptable utilization properties. With the exception of the bubble generators the converters cannot be used as actuators so that their utilization in connection with switching elements is limited. Because of the required heat fluctuations the processing media are exposed to significant thermal stress; in case of freezing elements also to mechanical stress.

Converters with gas formation are unsuitable for many microfluidic processes because most of them are gas bubble sensitive.

The object of the invention is to provide an LOC device that can be produced with an economically acceptable manufacturing expenditure and that automatically performs certain chemical, biochemical or other processes, in particular standard processes.

SUMMARY OF THE INVENTION

According to the invention the object is solved by a microfluidic processor with integrated active elements for handling process media that is characterized in that a) the active elements act by changes in their volume, swelling degree, material composition, their strength and/or viscosity, b) the procedures to be performed are defined already by the constructive configuration of the microfluidic processor
   - by an appropriate logic connection of the individual active elements defined in their function,
   - by the sequence of the temporal activation of the individual elements and
   - with respect to their processing speed and their precision, c) the process is enabled by action of a substantially non-directional collectively acting environmental parameter, in particular, the presence of a solvent and/or environmental temperature.

The basic principle of the invention resides in that by means of the microfluidic processor all required active process steps can be processed in a timely, qualitatively and quantitatively predefined sequence substantially automatically and without the use of auxiliary energy. For this purpose, the steps that require mechanical work to be performed, are performed automatically by components that are based on actuator-caused or strength-based property changes of certain materials. In this connection, these components are defined in their basic functions, the temporal and actuator behavior and are connected to one another to the appropriate logic functions.

By eliminating auxiliary energy as much as possible, an automated process sequence, pre-stocking with required materials (for example, analytes, reagents, auxiliary media) as well as an easily manipulatable size of the LOC, the process takes place substantially independent of the user in the quality that is predefined by the LOC manufacture and this process can be performed at any site. The user interaction is limited to introducing the sample, starting the process, and possibly reading the results. Therefore, the LOCs according to the invention also enable non-experts to perform complex examinations. Since the LOC configurations are very simple and built on the basis of only a few materials (mostly polymers), they can be produced inexpensively and can be used as a disposable product.

The material basis of the present invention is found in materials that can effect active functions by changing their swelling state or their mechanical properties (strength, viscosity) and that can be activated by means of easily realizable environmental parameters. Environmental parameters that are especially easily affected are the presence of a solvent as well as the temperature; therefore, they are of special importance for the present invention. Materials that by temperature action can be affected with regard to their strength or viscosity properties are, for example, oils and fats, waxes, paraffins, and alkanes. Semi-solid paraffins or soft paraffins have, for example, melting temperatures between 45° C. and 65° C., petrolatum and vaseline have melting temperatures in the range of 38° C. and 60° C.

Affected by the presence of a solvent are soluble materials, for example, non-crosslinked polymers, salts and organic natural materials such as saccharides.

Hydrogels can be influence by temperature as well as by the presence of solvent. As a result of the multitude of functions that can be realized by these materials, the invention will be explained in an exemplary fashion with the aid of hydrogels as a representative of other materials. Hydrogels are polymer networks that upon action of aqueous swelling media change their volume, their strength and other properties. These polymer networks can be divided, based on the type of polymer chain linkage with one another, in chemically and physically crosslinked polymer networks or hydrogels. In case of chemically crosslinked polymer networks, the individual polymer chains are linked irreversibly by covalent (chemical) connections. In case of physically crosslinked polymer networks the polymer chains are linked by physical interactions that mostly can be dissociated again.

When hydrogels swell from the dry state or de-swelled state, they not only change their volume but also, by generating a swelling pressure, can perform at the same time mechanical work. Physically and chemically crosslinked hydrogels exhibit these swelling properties. Certain chemically crosslinked hydrogels, the so-called stimuli-responsive hydrogels, can be transferred additionally, upon action of certain environmental parameters, reversibly again into the de-swelled state. This property is based on their volume phase transition behavior. Especially interesting are temperature-sensitive hydrogels such as poly(N-isopropyl acrylamide) and poly(methyl vinyl ether) that by appropriate absorption may also be “light-sensitive”. Most temperature-sensitive stimuli-responsive hydrogels have a lower critical solution temperature (LCST) characteristic, i.e., at low temperatures they are swollen and de-swell when surpassing the phase transition temperature. The best-known hydrogels with LCST characteristic, poly(N-isopropyl acrylamide) (PNIPAAm), has a volume phase transition temperature of 32.8° C. The position of the phase transition temperature or switching temperature of NIPAAm-based hydrogels can be adjusted by copolymerization and variation of the synthesis parameters in a range of +5° C. and approximately 60° C. Possible synthesis methods and structuring methods of PNIPAAm-based hydrogels are, for example, disclosed in A. Richter et al., *J. Microelectromech. Syst.* 12 (2003) 5, pp. 748-753.

Physically crosslinked hydrogels can also be temperature-sensitive. Such “thermoreversible” gels have a sol-gel transition behavior, i.e., upon reaching critical temperatures they gel (crosslink) or dissolve by de-crosslinking. Typical temperature-switchable physically crosslinkable hydrogels are, for example, gelatin, pectin, and agarose. Their sol-gel transition temperatures can be adjusted by various measures between approximately 15° C. and 95° C. An overview in regard to these and additional physically crosslinkable polymer networks is provided by K. te Nijenhuis, Thermoreversible Networks, Adv. Polym. Sci. 130, Springer-Verlag Berlin, Heidelberg, N.Y. 1997.

The temporal behavior of active hydrogel-based elements can be affected by appropriate selection of synthesis parameters and crosslinking parameters (thus in the end by selection of the hydrogel), by limitations of the swelling medium supply as well as forces that counteract the swelling process. The limitations regarding the supply of the swelling medium can be realized especially easily. This can be done by determining a corresponding flow resistance, for example, by selecting an appropriate effective flow cross-section across a material porosity. In this case, the swelling process is slowed down. A temporal delay of the beginning of the swelling process is achievable by employing swelling medium barriers that will dissolve after a certain period of time. The delay time can be defined by variation of the layer thickness as well as by material selection. Typical materials for swelling medium barriers or diffusion barriers are saccharides.

The first advantage of hydrogels relative to other converters resides in the enormous multitude of active functions that can be realized with them. They can be used as active fluidic elements in the form of switching elements, fluidic drives, uptake systems and release systems of active ingredients and of other compounds but also for enclosing/fixing or releasing objects (for example, by gelling or dissolving). A further advantage of these effect carriers is their simple manufacture. Hydrogels as plastic materials can be realized with the methods that are typical for this type of material. Since most of the functional elements also have the same or similar basic structures, the active hydrogel elements can be produced with one or only a few additional manufacturing steps directly on the channel structure supports.

BRIEF DESCRIPTION OF THE DRAWINGS

The invention will be explained with the aid of embodiments in more detail wherein the employed reference numerals have the same meaning throughout. The attached drawings show in:

Based on FIG. 1 first in an exemplary fashion a procedure will be explained that can be realized with the microfluidic processors according to the invention. FIG. 2 shows a possible configuration principle as well as some manufacturing possibilities and the principal function. FIG. 4 to FIG. 6 illustrate the function of some automated active hydrogel elements. FIG. 7 demonstrates further typical applications of the LOC according to the invention.

The microfluidic processor according to the invention with integrated active elements for handling process media is characterized in that a) the active elements (1,2,5,14,15,17,22,25)act by changes in their volume, swelling degree, material composition, their strength and/or viscosity, b) the procedures to be performed are defined already by the constructive configuration of the microfluidic processor
   by an appropriate logic connection of the individual active elements defined in their function,
   by the sequence of the temporal activation of the individual elements, and
   with respect to their processing speed and their precision, c) the process is enabled by action of a substantially non-directional collectively acting environmental parameter, in particular, the presence of a solvent and/or environmental temperature.

The microfluidic processor according to the invention is characterized in that the active elements (1, 2, 5, 14, 15, 17, 22, 25)are comprised of hydrogels that are chemically crosslinked and may be physically crosslinkable. The active elements are: (1 ) pump unit for receiving liquid; (2 ) pump unit for variation of mixing ratios; (5 ) valve unit; (14 ) active hydrogel element; (15 ) swelling medium barrier or diffusion barrier, blocking layer; (17 ) hydrogel actuator; (22 ) hydrogel valve; (25 ) pump chamber with culturing medium.

Figure 1:
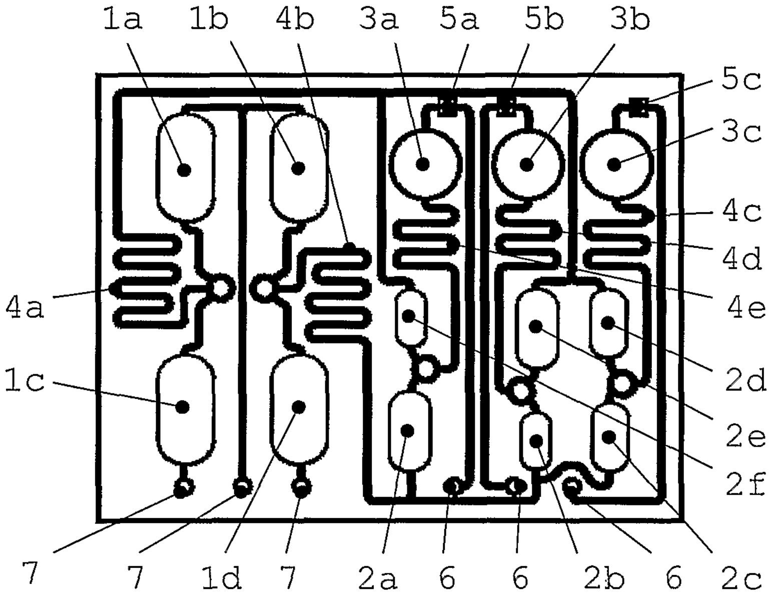
FIG. 1 the circuit diagram of the channel structure support of an automatic hydrogel-based microfluidic processor that, for example, can be used in the control of bioreactors based on the expression level of selected growth markers.

The circuit diagram illustrated in FIG. 1 of an LOC channel structure is suitable for several chemical, biotechnological and medical standard applications. Its functionality is explained with the aid of the determination of enzyme activity (laccase activity) of a bioreactor. In two pumps 1*a* and 1*b* there are 0.05 M malonate buffer at pH 5.0. A further pump 1*c* contains 2 mM of 2,2'-azino-bis(3-ethyl benzothiazoline-6-sulfonic acid) (ABTS) solution, functioning as a substrate, in an 0.05 M malonate buffer of pH 5.0. In another pump 1*d* there is a sample of a bioreactor product laccase that is, for example, removed from the ongoing reactor operation.

By simultaneously pumping the pumps 1*a* and 1*c* as well as the pumps 1*b* and 1*d* the buffer and substrate (pump 1*a* with pump 1*c*) as well as the buffer and sample (pump 1*b* with pump 1*c*) are mixed by means of mixing meander structures 4*a*, 4*b* and distributed onto pumps 2*a* to 2*f* wherein in the pumps 2*a* to 2*c* a buffer-sample mixture and in the pumps 2*d* to 2*f* a buffer-substrate mixture are provided, respectively. The pumps 1*a*-1*c* and 2*a*-2*f* each can be provided at the outlet with valves, not illustrated in detail, that in the presence of the liquid (which is the case when the pump chamber is completely filled) will automatically close and later on will open again when the pumping action begins.

By simultaneous actuation of the pumps:
2*a* and 2*f* (mixing ratio 2:1)
2*b* and 2*e* (mixing ratio 1:2)
2*d* and 2*c* (mixing ratio 1:1)
buffer-substrate and buffer-sample are mixed by further mixing meander structures 4*c* to 4*e* and transported into reaction units or analysis units 3*a* to 3*c*. Here, the enzyme reaction can be followed by means of optical analysis methods. As the simplest optical analysis unit a light-sensitive resistor (LDR—light-dependent resistor) can be provided, not illustrated in detail, that provides a simple yes/no response (enzyme activity present or not present). Enzyme-kinetic parameters can be determined by light-spectroscopic methods (for example, UV-VIS spectroscopy.

The basic media such as buffer and substrate can be introduced in a last manufacturing step during the LOC production. After prescribed storage, the user must only introduce the sample into the LOC and activate it. The entire procedure is then performed automatically.

By arranging in parallel several such LOCs a shorter cycle time of the enzyme activity control which corresponds to enzyme production control can be achieved.

Figure 2:
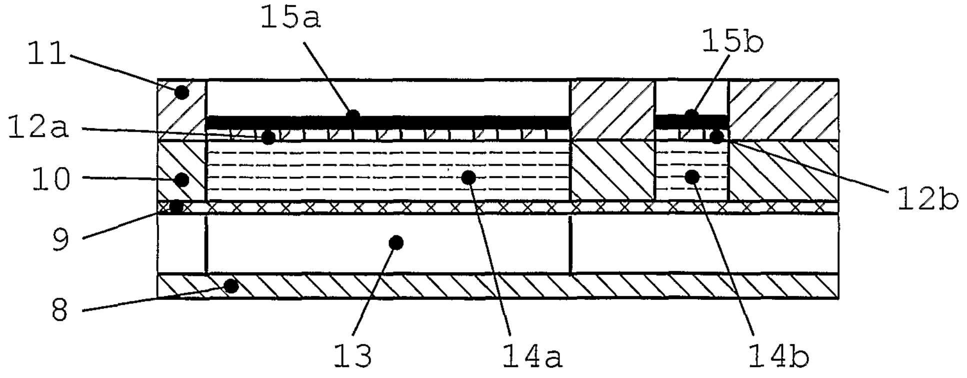
FIG. 2 the principal configuration of an automatic microfluidic processor in section illustration.

FIG. 2 represents a possible LOC configuration. The four-layer construction is comprised of a channel structure support 8 that is covered by a membrane 9 that is at least locally flexible. On top there is the actuator structure support 10 that contains a major proportion of the active hydrogel elements 14. Above the actuator structure support 10 there is a structure support 11 that supports the components 12, 15 with which the temporal sequence as well as the temporal behavior of the active hydrogel elements 14 are determined.

The production of the microfluidic processors according to the invention can be realized for the structure supports 8, 10, 11 with the conventional methods of mass production of shaped plastic parts such as injection molding, hot forming or the like. Suitable materials are those materials that are conventional in microfluidic applications, for example, polycarbonate (PC), cycloolefins (COC), polyamides (PA), polyesters (PES), polystyrene (PS), polyvinylchloride (PVC), polydimethylsiloxane (PDMS), polymethylmethacrylate (PMMA) or also polytetrafluoroethylene (PTFE).

For manufacturing small series or a unique specimen, methods of rapid prototyping, for example, milling of the channel structure, are suitable. A rather simple variant for manufacturing small series is PDMS master patterning. In this method, negative structures of the structure supports 8, 10, 11 are generated photolithographically in silicon wafers and these are subsequently coated with Teflon by sputtering in order to achieve excellent molding action. Subsequently, PDMS is applied to the molds and cured for an hour at 100° C.

The flexible membranes 9 can be produced of PDMS by rotary coating. The layer thicknesses can be adjusted very well with this method between approximately 15 μm to 100 μm. Films of the required thicknesses however are also commercially available.

The individual layers of LOC can be glued together, welded together or joined by force-fitting. Shaped PDMS parts can be adhesively connected very well, for example, after low pressure oxygen plasma treatment, with PDMS as an adhesive and subsequent heat curing.

The active hydrogel elements 14 can be produced by various methods. For structuring hydrogel layers the crosslinking photo-polymerization and photo-crosslinking reaction (A. Richter et al., *J. Microelectromech. Syst.* 12 (2003) 5, pp. 748-753) can be used. Furthermore, casting with subsequent polymerization as well as production of hydrogel particles (K.-F. Arndt et al., *Polym. Adv. Technol.* 11 (2000), pp. 496-505) are possible.

FIG. 2 shows an LOC detail with two active hydrogel elements 14*a*, 14*b* with which the principal function of the LOCs according to the invention can be described. The hydrogel elements 14*a*, 14*b* perform their task by expansion as a result of swelling in the channel structure of the structure support 8. The swelling medium required for this purpose is supplied to them via the structure support 11. The structure support 11 contains components that enable the predetermination of temporal behavior of the hydrogel elements 14. The swelling medium barriers 15*a*, 15*b* determine the point in time at which the swelling medium will reach the hydrogel elements 14. When the diffusion barriers are comprised, for example, of the same material wherein however 15*b* is thinner than 15*a*, 15*b* will dissolve faster than 15*a* and the hydrogel element 14*b* begins to act before 14*a*. On the one hand, the semipermeable walls 12*a* and 12*b* serve as a solid support for the hydrogel elements 14, and, on the other hand, by variation of the effective supply cross-section, they define also the maximum possible volume expansion of the elements 14 per time unit. The arrangement can serve, for example, as a sample receiving unit. Through the side of the element 14*b*, the pump chamber 13 can be filled with sample liquid. After a certain time in the filled state has elapsed, the diffusion barrier 15 is dissolved so that the swelling medium reaches the hydrogel elements 14*b* and the latter will swell. 14*b* closes off the channel structure as a result of deflection of the membrane 9. After the barrier 15*a* has dissolved, the element 14*a* displaces by means of the flexible membrane 9 the liquid from the pump chamber 13 of the structure support 8 in the direction of the exit that is not closed.

Figure 3A:
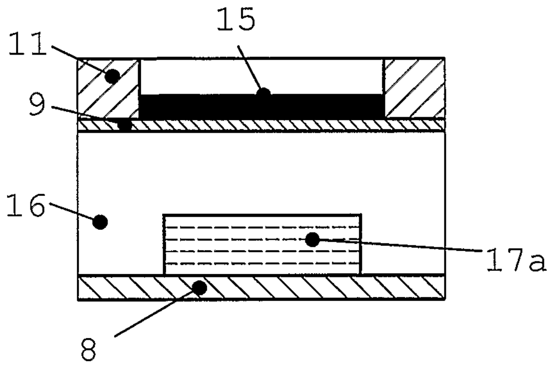
FIG. 3*a* to FIG. 3*c* the principal function of a time-controlled and event-controlled valve.
Figure 3B:
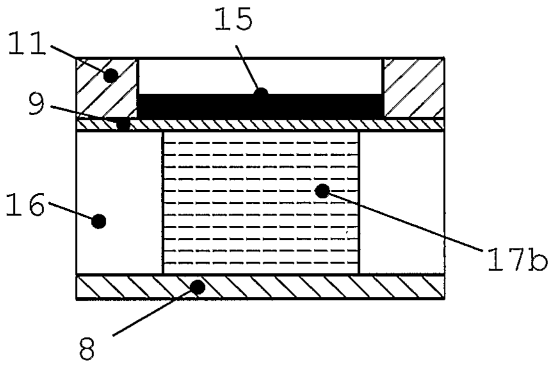
Figure 3C:
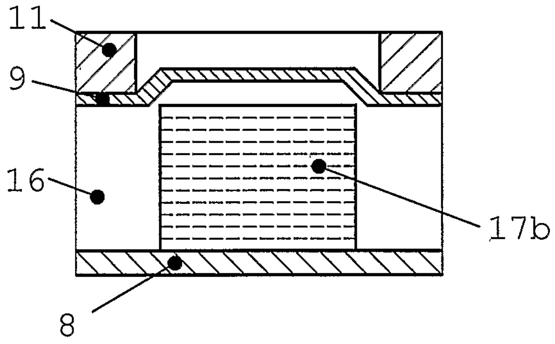

In addition to the time control explained in connection with FIG. 2, the entire task sequence of the LOC or individual tasks can also be activated or processed based on an event. In this connection, it is possible that individual components must be activated several times. FIG. 3, for example, represents a valve that first is actuated event-controlled and then time-controlled. A frequent task is to close a storage structure or a channel structure after completion of filling with the processing medium. When the medium contained in the channel 16 reaches the hydrogel actuator 17*a* that is not swelled (FIG. 3*a*), the latter will begin to swell by taking up the processing medium until the channel structure 16 is completely closed by it (swelled hydrogel actuator 17*b* in FIG. 3*b*). The take-up of the processing medium by 17*b* as a result of its swelling can happen so quickly that no medium can flow past the valve seat. The opening action of the valve is time-control. As illustrated in FIG. 3*c*, after elapse of the preadjusted time the blocking layer 15 is dissolved or is impaired with regard to its strength such that the flexible membrane 9 at the valve seat will deflect and therefore will open the valve seat.

Adequate results may be obtained with several mechanisms that are based on the change of the swelling degree, the strength or viscosity or the crosslinking properties of the functional elements. Of course, it is also possible to trigger certain components several times only by time control or only by event control.

Figure 4A:
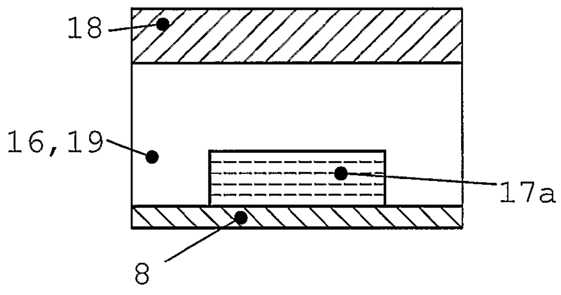
FIG. 4*a* to FIG. 4*c* the principal function of a time-controlled and event-controlled valve on the basis of a thermoreversible physical polymer network.

The component function as disclosed in connection with FIG. 3 can also be realized by the functional principle illustrated in FIG. 4. As a material, a thermoreversible physical polymer network is utilized while the temperature serves as the parameter that triggers the opening procedure.

Figure 4B:
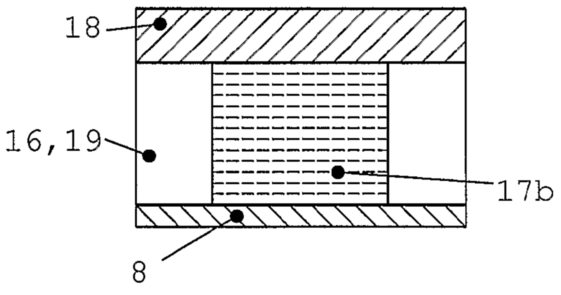
Figure 4C:
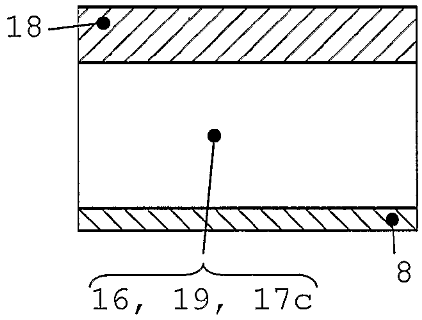

When the process medium 19 within the channel 16 impinges on the hydrogel actuator 17*a* that is not swelled (see FIG. 4*a*) the latter will swell by taking up the processing medium 19 until the channel 16 is completely closed off by it (FIG. 4*b*). After reaching a certain temperature (this can be realized event-controlled or time-controlled) the physical polymer network will de-crosslink and dissolve (17*c* in FIG. 4*c*). In this way, the channel 16 is opened and the medium can therefore be transported farther. This temperature can be realized possibly by fever or inflammations.

Figure 5A:
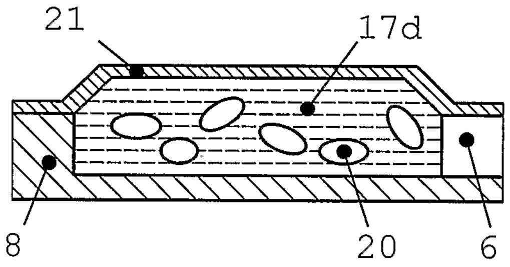
FIG. 5*a* and FIG. 5*b* the function of an active ingredient dispensing unit on the basis of a dissolvable element.
Figure 5B:
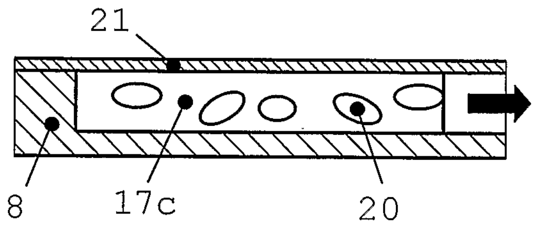

FIG. 5 represents a device that can release active ingredients. In a chamber of the structure support 8 there is an active ingredient 20 which is enclosed in a matrix of the gelled hydrogel 17*d* (FIG. 5*a*). Channel structure support 8 and the chamber with 17*d* and 20 is covered by an elastic film that is pretensioned across the chamber and therefore serves as a spring force storage device. The gelled hydrogel 17*d* may be thermoreversible. The active ingredient 20 is released when the gelling temperature of the hydrogel has been reached and the hydrogel (17*c* in FIG. 5*b*) dissolves. By dissolving the mechanical resistance, the spring force storage device 21 is released and presses the dissolved substances through the outlet 6 out of the chamber.

Figure 6A:
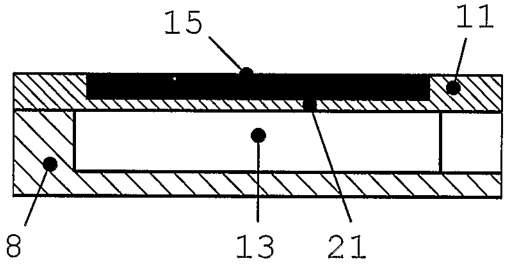
FIG. 6*a* and FIG. 6*b* the function of a component that serves as a lock of a spring force storage device.
Figure 6B:
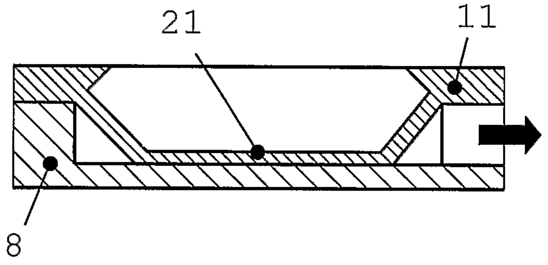

FIG. 6 shows that an activation of spring force storage devices can be realized also in a simple way by a programming unit 11. A pre-stressed spring force storage device 21 is locked in this position by a blocking layer 15 (FIG. 6*a*). When the blocking layer 15 is dissolved by the presence of a solvent or its strength is reduced, the spring force storage device can discharge in that it deflects into the chamber 13 and displaces the medium that is contained therein (FIG. 6*b*).

The time-dependent control or also the event-dependent control of the LOC processes can be realized, aside from the presence of swelling medium, also by changing the environmental temperature or LOC temperature.

For example, the temperature that acts as a control can be increased continuously by a defined heating rate. When the individual components are provided with different activation temperatures (for example, gelling temperature, phase transition temperature), they are activated according to a corresponding temperature-staged sequence. Moreover, with an appropriate adjustments of the temperature also the kinetics in the sense of velocity at which the processes are performed can be influenced.

Since the variation of the activation temperatures of the individual components may lead possibly to an undesirably high multitude of materials, the sequence of components with same activation temperature can be realized by an appropriate thermal dimensioning of the LOC configuration in that heat resistors (variation of the heat conductivity, the material thickness etc.) that act as series resistors as well as the heat capacities are predetermined. In this connection the components that are provided with a comparable minimal heat resistance are triggered first because they reach their activation temperature first.

An event-dependent temperature control of the LOC or certain functions is recommended when temperature-controlled devices must be utilized anyway as is the case, for example, in connection with polymerase chain reactions (PCR). After completion of PCR the required components can be controlled by a short heating power increase by means of the PCR heating unit. Such devices may be, for example, appropriately modified PCR thermodevices, thermostats, thermocyclers, heating cabinets or heating baths that are capable of realizing predetermined temperature programs.

In medicine and in biochemistry with a different weighting, there are four diagnostic-analytical focuses: blood chemistry, antigen-antibody reactions, nucleic acids amplification tests, and cytometry. Nucleic acid amplification tests such as PCR are generally superior with respect to sensitivity and selectivity to the two other widely used possibilities for identification of microorganisms, immunoassays and culturing methods. The two latter are however much simpler to realize and therefore are especially interesting with regard to the present invention. In the following, first a PCR-based LOC and subsequently and LOC according to the culturing method will be presented.

Figure 7:
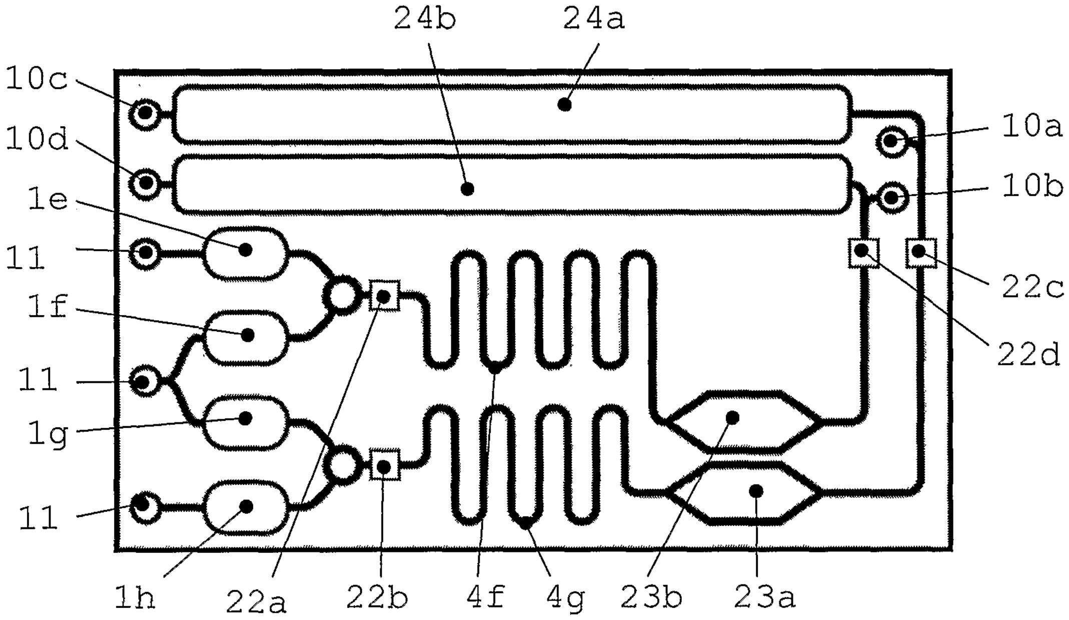
FIG. 7 a possible circuit diagram of a LOC configuration for biochemical and medical standard applications that are based on polymerase chain reactions.

FIG. 7 shows a circuit diagram of an LOC configuration for biochemical and medical standard applications that are based on polymerase chain reactions. For the polymerase chain reaction a master mix, a template DNA for the control reaction (template DNA1) and a template DNA for the actual PCR reaction (templates DNA2) are provided.

The master mix can have, for example, the following composition:

4 μl 10× buffer with 25 mM $MgSO_4$ (10× Pfu polymerase reaction buffer, Fermentas Life Science)

0.2 μl forward primer (FP) final concentration 1 μm 0.2 μl reverse primer (RP) final concentration 1 μm 3.2 μl dNTP (deoxyribonucleoside triphosphate mixture; Fermentas Life Science) final concentration 0.4 mM each 0.8 μl Pfu-DNA-polymerase (2.5 u/μl; Fermentas Life Science) and 11.6 μl $H_2O$ (molecular biology grade).

As needed, $H_2O$ can also be substituted proportionally by additives such as DMSO, glycerin, and others (for example, in case of high GC content).

For multiple applications the volume specifications for the master mix are multiplied by the number of applications. The thus prepared master mix can be provided in a cooled storage vessel (4° C.) outside of the LOC. The same holds true for the template DNAs.

The pumps 1*f* and 1*g* are loaded with 10 μl each of a master mix. The pump contains 10 μl of template DNA1 (plasmid, approximately 100 ng in $H_2O$—molecular biology grade) for the PCR control reaction. Pump 1*e* contains 10 μl template DNA2 (plasmid, approximately 100 ng in $H_2O$—molecular biology grade) for the PCR reaction.

By simultaneously pumping the pumps 1*e*, 1*f*, 1*g*, 1*h*, 10 μl of the master mix are mixed with 10 μl template DNA1 (pump 1*h* and pump 1*g*) and 10 μl master mix are mixed with 10 μl template DNA2 (pump 1*e* and pump 1*f*) through the mixing meander structures 4*f* and 4*g* and, after opening of the hydrogel valves 22*a* and 22*b*, are transported to the PCR chambers 23*a* and 23*b*. In the chambers 23*a* and 23*b* the polymerase chain reactions are carried out wherein the temperature programs can be realized by an external thermocycler. A possible PCR temperature program can be carried out as follows:

5 minutes at 94° C. (initial template denaturing)

30 cycles 30 seconds each at 94° C. (template denaturing) and 30 seconds at 55° C. (primer annealing)

4 minutes at 72° C. (primer elongation).

Subsequently, incubation for 5 minutes at 72° C. for completing the primer elongation is carried out.

After PCR by simultaneously pumping the pumps 1*e* to 1*h* and opening of the hydrogel valves 22*c* and 22*d*, the PCR products are transported into the gel electrophoresis chambers 24*a*, 24*b* (usually agarose gel electrophoresis) wherein onto the gel of 24*a* the PCR products of the control reaction and onto the gel of 24*b* the PCR products of the actual PCR are applied.

As needed, the PCR products can also be removed at the outlet 10*a* or outlet 10*b* for external further processing.

By applying a voltage (field strength of 10 V/cm) the PCR products in the chambers 24*a* and 24*b* are electrophoretically separated and can be made available at the outlet 10*c* and the outlet 10*d*, for example, for external fluorescence analysis. 11 refers to the inlets to the pump chambers 1*e* to 1*h*.

By adjusting the master mix composition (several primers) and the template DNA (sample DNA) this principal configuration can be applied to multiple DNA analysis methods. Any application based on the principle of PCR DNA analysis, for example, DNA fingerprint (paternity test), virus analysis and others, can be realized on the LOC.

By adjusting the architecture (for example, additional pumps, mixing chambers, reaction chambers etc.) also more complex sequences as they are required for example for reverse transcriptase PCR (RT-PCR) can be realized on an LOC. In this context, it is only necessary to compose an RT master mix and to integrate a further temperature program before PCR (two-step RT-PCR method). Alternatively, of course also the configuration described in connection with FIG. 5 can be used in connection with a one-step RT-PCR method.

The principle composition of an RT master mix for a two-step RT-PCR method is disclosed in the following example:

total RNA or mRNA (prokaryotic or eukaryotic) with the target sequence reverse transcriptase(s)

dNTPs (compare PCR)

oligo(dT)-primer (alternative: sequence-specific or random-hexamer primer) and

RNase inhibitor in the correlated transcriptase buffer.

The cDNA synthesis is performed at 37° C. to 50° C.

Figure 8:
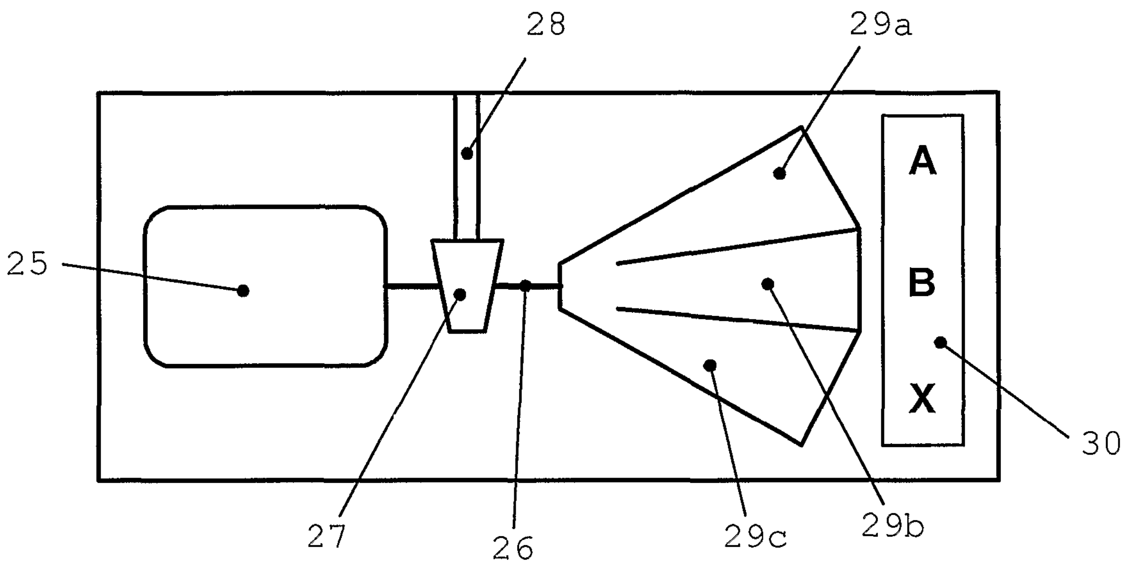
FIG. 8 a possible LOC circuit diagram for biochemical and medical standard applications that are based on the culturing method.

FIG. 8 shows an LOC configuration in which in simple way according to the culturing method microorganisms are identified or excluded in a simple way. A smear swab is inserted through the sample channel 28 into the sterile sample receptacle chamber 27. The smear material is stripped off so that the microorganisms that are present remain at 27. At the same time, by a mechanism, not illustrated in detail, the pump 25 is activated so that the culturing medium flows through the channel 26 by entraining the smear material into the analysis chambers 29*a* to 29*c*. In the analysis chambers 29 there are selective culturing media that enhance or inhibit the growth of certain organisms or, as a result of their composition, change their properties as a function of the microorganisms growing thereon (for example, change color). After a predetermined time the grown cultures or the color change is visible for a positive test and can be read by the user. The labeling 30 serves for providing the user with a definite correlation of the analysis results.

A corresponding result can also be obtained for the antigen/antibody reactions, by specific enzymes or with other molecular-specific reactions.

Applications in medicine are, for example, smears for differentiating fungal or bacterial infections. An expanded differentiation is, for example, expedient in case of frequently occurring disease classes such as sexually transmitted infections STI such as gonorrhea (*Neisseria gonorrhoeae*), syphilis (*Treponema pallidum*), chancroid (*Haemophilus ducreyi*), chlamydia (*Chlamydia trachomatis*) or regionally typical diseases (for example, malaria, hepatitis, HIV, typhoid fever, measles, influenza, dengue fever). In the field of hygiene, for example, *Escherichia coli* can be detected in toilets, hospital beds, showers etc. Also, microbial loading of foodstuffs and the environment, for example, *legionella* (*Legionella pneumophila*) in drinking water or *salmonella* in foodstuffs can be detected by the LOCs in a simple way.

The discussed embodiments represent a plurality of possible further applications of the microfluidic processors according to the invention. By adjustment of the processor architecture (for example, additional pumps, mixing chambers, reaction chambers etc.) also more complex sequences can be realized on an LOC. Multiple pipetting and analysis tasks can be miniaturized and automated; this not only effects a significant cost reduction and time reduction but also improves significantly the processing quality, for example, by reducing pipetting errors. The LOCs are preferably suitable for a one-time procedure (disposable article) but, when appropriately designed, can be used in connection with continuous or on-line tasks. As a result of miniaturization and automation a mobile (energy) independent and site-independent use of the LOCs is possible. No additional analytical units and reading units are required because of the easily observable property changes.

In the field of biotechnology, they are, for example, suitable for enzyme reactor or bioreactor monitoring inter alia for prokaryotes, eukaryotes, yeasts and fungi. A rapid screening of the activity of enzymes of different enzyme classes can be realized. By combination of several LOCs, multi rapid screening can be made possible.

In environmental analysis and water analysis, for example, microorganism analyses can be realized by detecting and correlating an activity profile but also quick tests for detecting water quality (COD—chemical oxygen demand), BOD (biological oxygen demand), heavy metals, nitrate, nitrite etc.

In the medical field the LOC technology according to the invention can be applied, for example, for cell culturing control (eukaryotes, human cell lines and others) by viability tests [for example, WST-1 test and MTT test (conversion of a tetrazolium salts in formazan, e.g. 4-[3-(4-iodophenyl)-2-(4-nitrophenyl)-2H-5-tetrazolium]-1,3-benzene disulfonate) or LDH test (lactate dihydrogenase test)] etc. In this way, cell quality control, batch control, and passage control for human cell lines is possible.

On-chip blood tests for detecting some of the most important blood analysis parameters, for example, blood sugar, pH value, lactate, minerals, creatine, hormones, enzymes, leucocytes, erythrocytes, and others, disease markers, the detection of reactive oxygen toxic substances (ROTS oxidative stress) etc., can be realized. In case of urine tests and fecal tests, for example, the presence of blood, sugar, leucocytes, and proteins can be examined.

LIST OF REFERENCE NUMERALS

1, 1*a*-1*h* pump unit for receiving liquid
2, 2*a*-2*f* pump unit for variation of mixing ratios
3, 3*a*-3*c* reaction units or analysis units
4, 4*a*-4-*g* mixing meander structure
5, 5*a*-5*c* valve unit
6, 6*a*-6*d* exit/outlet
7 intake/inlet
8 channel structure support
9 flexible membrane
10 actuator structure support
11 structure support of the programming unit
12, 12*a*-12*b* semipermeable wall
13 pump chamber
14, 14*a*-14*b* active hydrogel element
15, 15*a*-15*b* swelling medium barrier or diffusion barrier, blocking layer
16 channel in the channel structure support
17 hydrogel actuator
17*a* de-swelled hydrogel actuator
17*b* swelled hydrogel actuator
17*c* dissolved hydrogel actuator
17*d* gelled hydrogel actuator
18 cover
19 processing medium
20 active ingredient
21 spring force storage device
22, 22*a*-22*d* hydrogel valve
23, 23*a*, 23*b* PCR chamber
24, 24*a*, 24*b* gel electrophoresis chamber
25 pump chamber with culturing medium
26 channel
27 sterile sample receiving chamber with stripping mechanism and trigger
28 sample channel
29*a*, 29*b*, 29*c* analysis chamber with selection medium
30 labeling

What is claimed is:

1. A microfluidic processor comprising:

a channel structure support with a channel structure;

an actuator structure support connected to the channel structure support;

first active elements arranged on the actuator structure support;

wherein the first active elements comprise a dry or de-swelled swellable polymer network and, upon actuation effected by exposing the dry or de-swelled swellable polymer network to a solvent, act on the channel structure in a timely, qualitatively and quantitatively predefined sequence substantially automatically and without use of auxiliary energy to open or close elements of the channel structure by changes of the first active elements in volume, swelling degree, material composition, strength and/or viscosity;

second active elements that are arranged on the actuator structure support and that dissolve after a certain period of time when exposed to the solvent and provide a temporal control of the predefined sequence of the first active elements, wherein the second active elements are in the form of swelling medium barriers or blocking layers.

2. The microfluidic processor according to claim 1, wherein the first active elements are comprised of hydrogels that are chemically crosslinked and may be physically crosslinkable.

3. The microfluidic processor according to claim 2, wherein the hydrogels or a polymer solution are based on gelatins or polysaccharides.

4. The microfluidic processor according to claim 1, wherein the second active elements comprise soluble materials that perform the function of locking, blocking, and supporting.

5. The microfluidic processor according to claim 4, wherein the soluble materials are saccharides or salts.

6. The microfluidic processor according to claim 4, wherein the swelling medium barriers are provided in different thickness or different material composition and, based on a difference in time for dissolving the swelling medium barriers, the swelling medium barriers enable the temporal control of the predefined sequence of acting on the channel structure.

7. The microfluidic processor according to claim 1, wherein the channel structure comprises channel structure elements that define at least two fluidic sequences, wherein each fluidic sequence comprises first pumps and second mixing pumps as channel structure elements, wherein a) in each fluidic sequence the first pumps premix different processing media in accordance with respective predetermined conveying volumes of the first pumps by appropriate connection at an outlet side of the first pumps and supply the different processing media to the second mixing pumps;

b) at least two second mixing pumps from different fluidic sequences are connected at their outlet, c) the at least two connected second mixing pumps represent a mixing ratio that is determined by the respective predetermined conveying volume of the at least two connected second mixing pumps, and d) at least two connected second mixing pumps supply the resulting mixture via outlets or convey the resulting mixture to analysis units or reaction units.

8. The microfluidic processor according to claim 7, wherein the mixing ratios of the first and second pumps are constructively predetermined by a respective size of the pump chambers of the pumps.

9. The microfluidic processor according to claim 7, wherein the channel structure comprises several mixing or supplying stages based on an appropriate connection of the first and second pumps.

10. The microfluidic processor according to claim 1, wherein the channel structure comprises pumps that define at least one fluidic sequence wherein the pumps premix various processing media in accordance with respective predetermined conveying volumes of the pumps by an appropriate outlet connection of the pumps and convey the resulting mixture to reaction units and analysis units.

11. The microfluidic processor according to claim 10, wherein the mixing ratios of the pumps are constructively predetermined by a respective size of the pump chambers of the pumps.

12. The microfluidic processor according to claim 10, comprising several mixing or supplying stages based on an appropriate connection of the pumps.

13. The microfluidic processor according to claim 1, adapted to detect an enzyme activity of a biochemical process.

14. The microfluidic processor according to claim 1, adapted to control and/or detect processes based on polymerase chain reaction.

15. The microfluidic processor according to claim 1, adapted to perform processes based on the culturing method.

16. The microfluidic processor according to claim 1, adapted to perform processes based on antigen-antibody reactions.

17. The microfluidic processor according to claim 1, further comprising an at least locally flexible membrane and a structure support.

* * * * *